United States Patent
Ahn

(10) Patent No.: US 9,919,001 B2
(45) Date of Patent: Mar. 20, 2018

(54) DRUG CARRIER HAVING L-DNA NANOCAGE STRUCTURE

(71) Applicant: Korea Institute of Science and Technology, Seoul (KR)

(72) Inventor: Dae-Ro Ahn, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/514,855

(22) Filed: Oct. 15, 2014

(65) Prior Publication Data
US 2016/0287706 A1    Oct. 6, 2016

(30) Foreign Application Priority Data
Nov. 18, 2013 (KR) .................. 10-2013-0140020

(51) Int. Cl.
| | |
|---|---|
| A61K 47/48 | (2006.01) |
| B82Y 40/00 | (2011.01) |
| C12N 15/11 | (2006.01) |
| A61K 31/704 | (2006.01) |
| A61K 31/7088 | (2006.01) |
| A61K 9/51 | (2006.01) |
| A61K 38/00 | (2006.01) |

(52) U.S. Cl.
CPC .......... *A61K 31/704* (2013.01); *A61K 9/5146* (2013.01); *A61K 31/7088* (2013.01); *A61K 38/00* (2013.01)

(58) Field of Classification Search
None
See application file for complete search history.

(56) References Cited

FOREIGN PATENT DOCUMENTS

| WO | WO2007122405 | * 11/2007 |
| WO | WO2013006411 A1 | * 1/2013 |

OTHER PUBLICATIONS

Jan Willem De Vries et al., Drug delivery systems based on nucleic acid nanostructures, Journal of Controlled Release, Jun. 3, 2013, p. 467-483, 172, www.elsevier.com/locatejconrel.
Kim et al., Drug Delivery by a self-assembled DNA tetrahedron for overcoming drug resistance in breast cancer cells, ChemComm, 2013, pp. 2010-2012, vol. 49, RSC publishing.
Korean Office Action dated Dec. 17, 2014 for Korean Application No. 10-20-14-0140020 which corresponds to instant application.
Goodman, R.P. et al., "Rapid Chiral Assembly of Rigid DNA Building Blocks for Molecular Nanofabrication" *Science* vol. 310, Dec. 9, 2005 pp. 1661-1665.

* cited by examiner

*Primary Examiner* — Christopher M Babic
*Assistant Examiner* — Kimberly A Aron
(74) *Attorney, Agent, or Firm* — Goldilocks IP Law

(57) ABSTRACT

The present invention relates to a drug carrier having L-DNA nanocage structure prepared by using L-DNA, the mirror form of natural DNA, as a backbone. The drug carrier of the present invention has very superior cellular uptake efficiency and serum stability, so that it can be applied to deliver various drugs into cells usefully.

11 Claims, 9 Drawing Sheets
(8 of 9 Drawing Sheet(s) Filed in Color)

(a)

(b)

(a)

Protein delivery by L-DNA tetrahedron (b)

Protein delivery (L-Td-Bt-Str)

(c)

under the US 9,919,001 B2

DRUG CARRIER HAVING L-DNA NANOCAGE STRUCTURE

CROSS-REFERENCE TO RELATED APPLICATION

This application claims priority from Korean Patent Application No. 10-2013-0140020 filed on Nov. 18, 2013 in the Korean Intellectual Property Office, the disclosure of which is incorporated herein by reference in its entirety.

BACKGROUND OF THE INVENTION

1. Field of the Invention

The present invention relates to a drug carrier having L-DNA nanocage structure and a pharmaceutical composition for treating cancer comprising the same.

2. Background of the Invention

DNA nanocarriers are an emerging class in drug delivery technologies. Differed from most of polymer-based carriers, they are fully biodegradable into non-toxic small nucleotides and easily controllable in size and shape at a tailor-made level.

Previously, it has been shown that biocompatible DNA could self-assemble to construct various three dimensional (3D) DNA nanocages including tetrahedra, bipyrimids, octahedra, dodecahedra and fullerene-like structures. Among them, the DNA tetrahedron has been considered one of the most practical DNA nanocages since it can be assembled simply from four DNA strands and prepared in high yield.

The recent demonstration about cellular uptake of the DNA tetrahedron into mammalian cells has opened a great opportunity for the nanocage to play important roles in biomedical applications. They are often internalized in mammalian cells in the absence of any transfection agent. These properties are valuable when they are employed in biomedical applications.

Recently, DNA nanocarriers have been utilized in intracellular delivery of bioactive molecules such as anticancer drugs, aptamers, antisenses, immunogenic molecules, and siRNA. DNA nanocarriers are particularly useful in delivery of nucleic acid cargos, since the vehicle and the cargo are the same nucleic acids and can thus be designed and prepared in an integrated feature without any conjugation chemistry. For the successful assembly of a cargo-loaded carrier, however, the sequences of the carrier and the cargo should be carefully designed and selected since not only the DNA nanocarrier but the oligonucleotide-based cargo also employs A-T and G-C base-paring patterns for construction of active motifs, which has a potential to disturb the self-assembly of the DNA nanocarrier. The probability of undesired assembly resulting from this interference would increase when more than one kind of nucleic acid-based cargos are attached to the carrier.

This application seeks priority to and incorporates by reference the following U.S. pending provisional patent applications. Methods and materials similar or equivalent to those described herein can be used in the practice or testing of embodiments of the present invention. All publications mentioned herein are incorporated by reference in their entirety. The documents, patents and patent applications referred to herein are hereby incorporated by reference.

SUMMARY OF THE INVENTION

Inventors of the present invention have studied and given effort to develop a noble biocompatible drug carrier having superior intracellular delivery efficiency and serum stability. As the results, they completed the present invention by identifying that L-DNA nanocage structure prepared using L-DNA, the mirror form of natural DNA, as a backbone had very superior intracellular intake efficiency and serum stability, so could be used helpfully to deliver various drugs into cells.

Thus, an object of the present invention is to provide a drug carrier having L-DNA nanocage structure where L-DNA forms 3 dimensional cage form.

Another object of the present invention is to provide a pharmaceutical composition for treating cancer comprising the drug carrier and an anticancer drug.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(b) Natural PAGE for identifying D-Td (left) and L-Td (right) assembly (c) DLS data of D-Td (left) and L-Td (right)

(d) CD spectrum of D-Td (blue) and L-Td (red) (2.5 µM).

Figure 2:
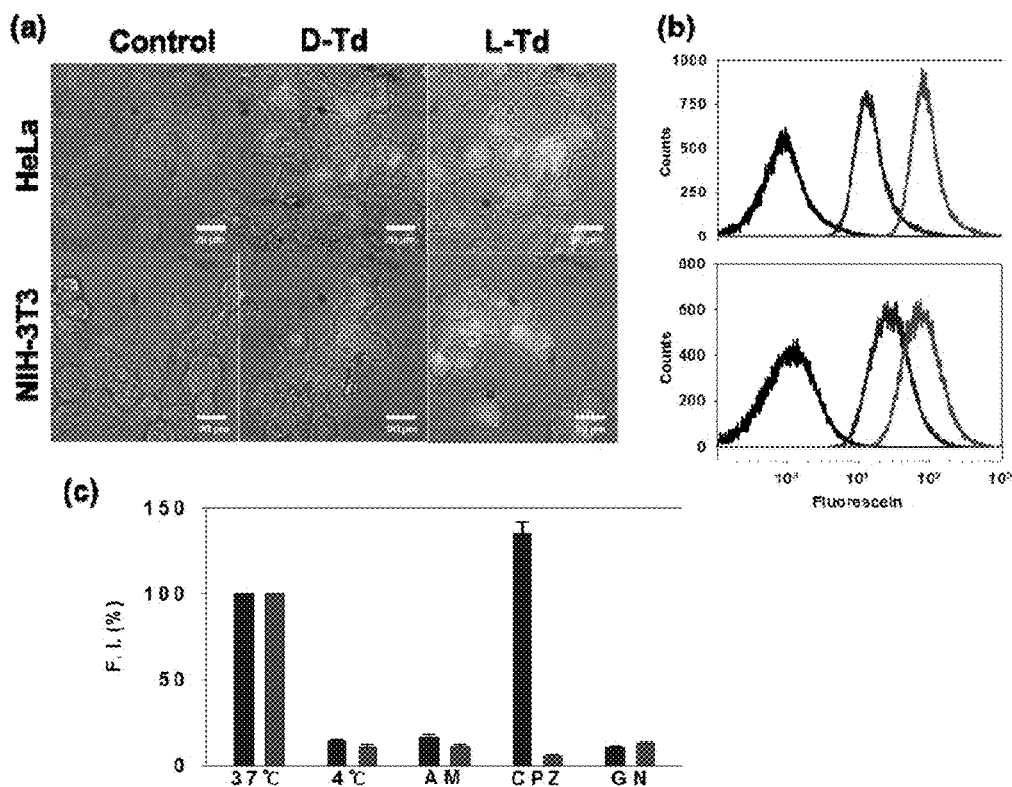

FIG. 2 (a) Fluorescence microscopic image of cancer cells (HeLa, top) and normal cells (NIH-3T3, bottom) treated with D-Td (left) and L-Td (right).

(b) Flow cytometry for cellular uptake of D-Td (blue) and L-Td (red) into HeLa (top) and NIH-3T3 cells (bottom). Black line indicates untreated cells.

Mean cellular fluorescence intensity of D-Td (blue) and L-Td (red) in Hela cell lysates from the cells cultured under presence of other types of endocytosis inhibitors (chloropromazine (CPZ), amiloride (AM) and genistein (GN)) The cellular fluorescence intensity was standardized into total cellular protein amount.

Figure 3:
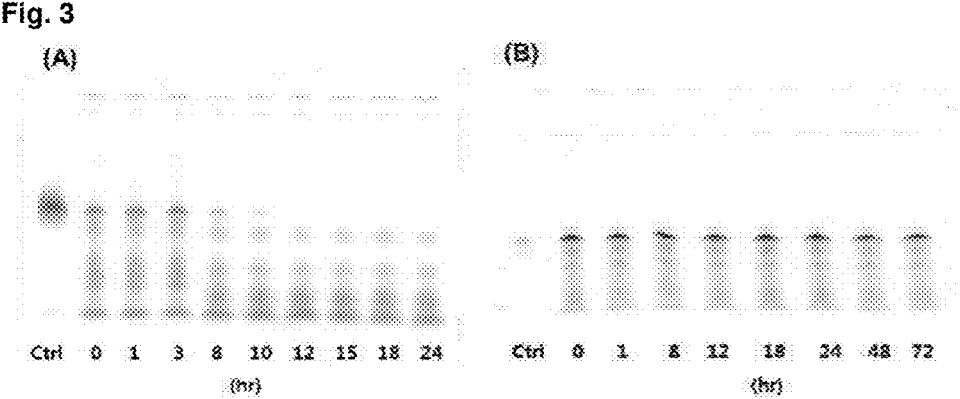

FIG. 3 Serum stability of D- and L-Td DNA Tds was cultured in 10% mouse serum. Control sample (Ctrl) was prepared without serum.

Figure 4:
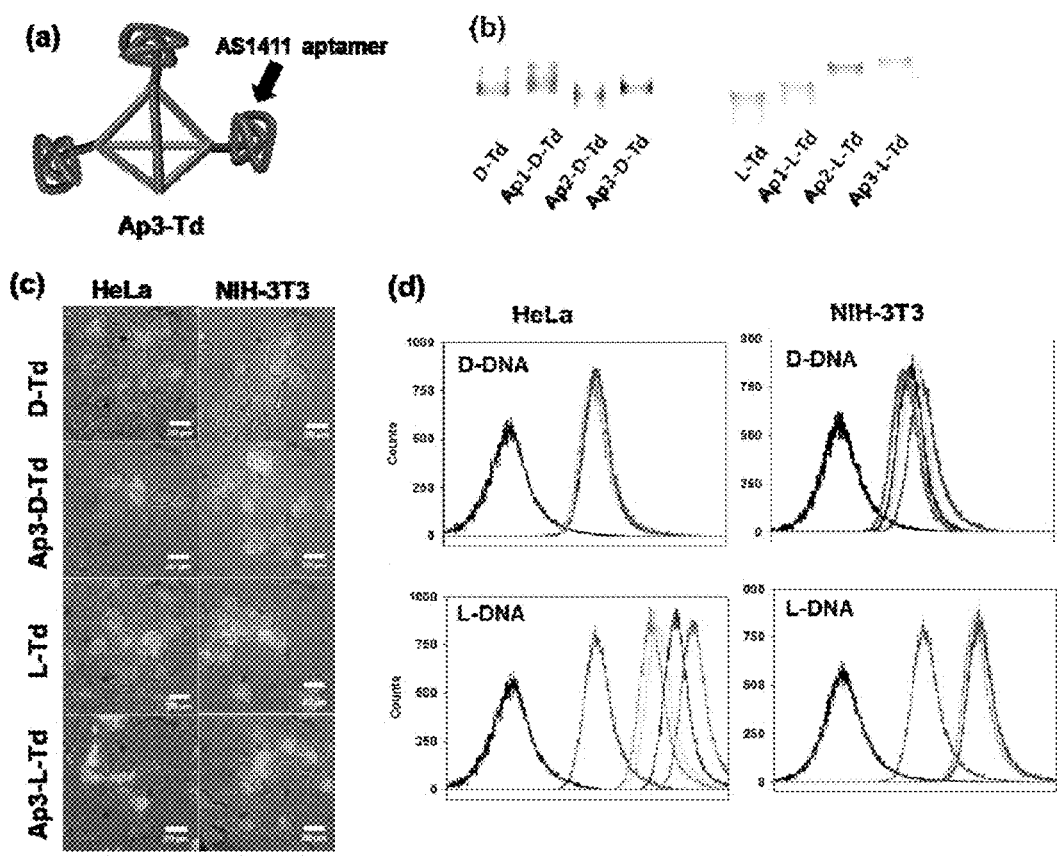

FIG. 4 (a) Diagram of 3 AS1411 aptamers attached Td.

(b) Natural PAGE for analyzing assembly of aptamer attached Tds.

(c) Cellular uptake of aptamer attached Tds into cancer and normal cells.

(d) Flow cytometry for cellular uptake of Td (green), Ap1-Td (orange), Ap2-Td (blue), Ap3-Td (magenta) and free AS1411 aptamer (red) into the cells. Black line indicates untreated cells.

Figure 5:
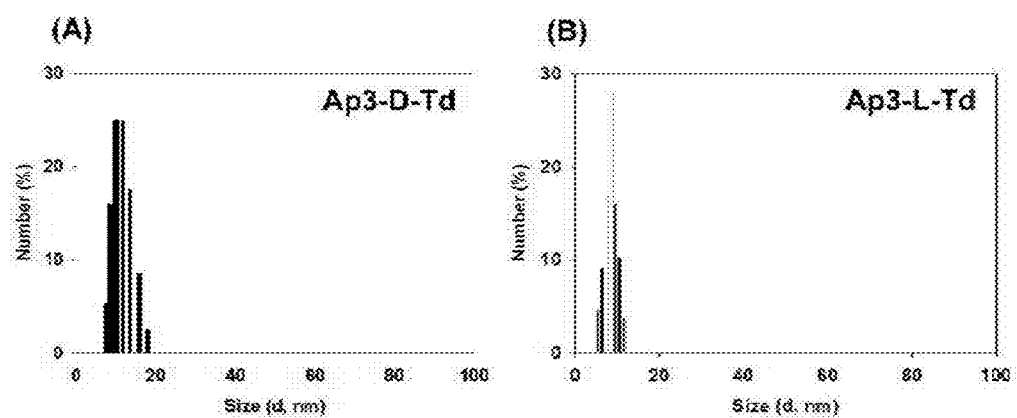

FIG. 5 Size of Ap3-D-Td(A) and Ap3-L-Td(B) measured by DLS.

Figure 6:
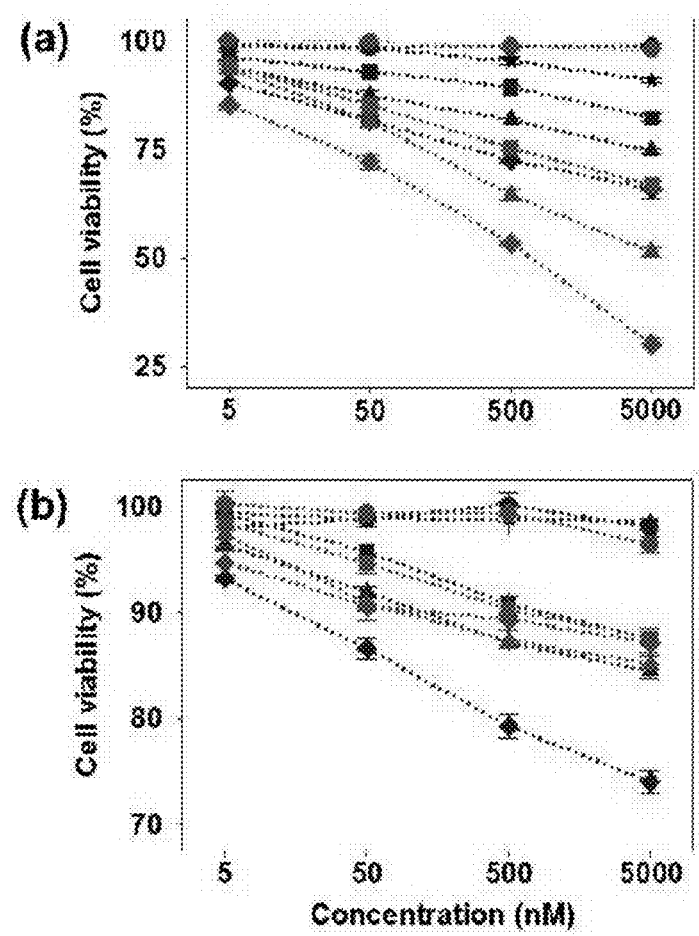

FIG. 6 Cytotoxicity of D-DNA-based construct (blue), L-DNA-based construct (red) and free AS1411 aptamer (black). Circular: Td, Square: Ap1-Td, triangle: Ap2-Td, diamond: Ap3-Td, star: free AS1411.

Figure 7:
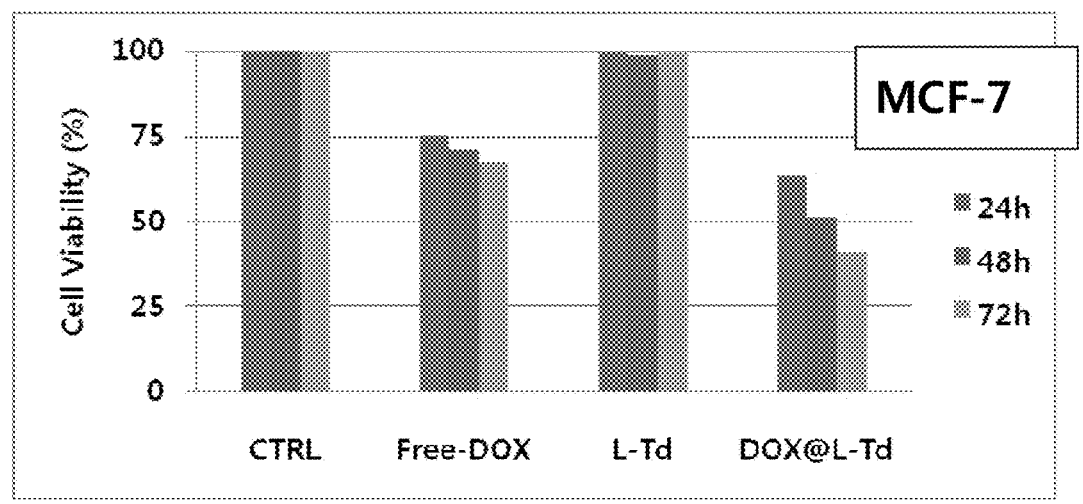
Figure 7:
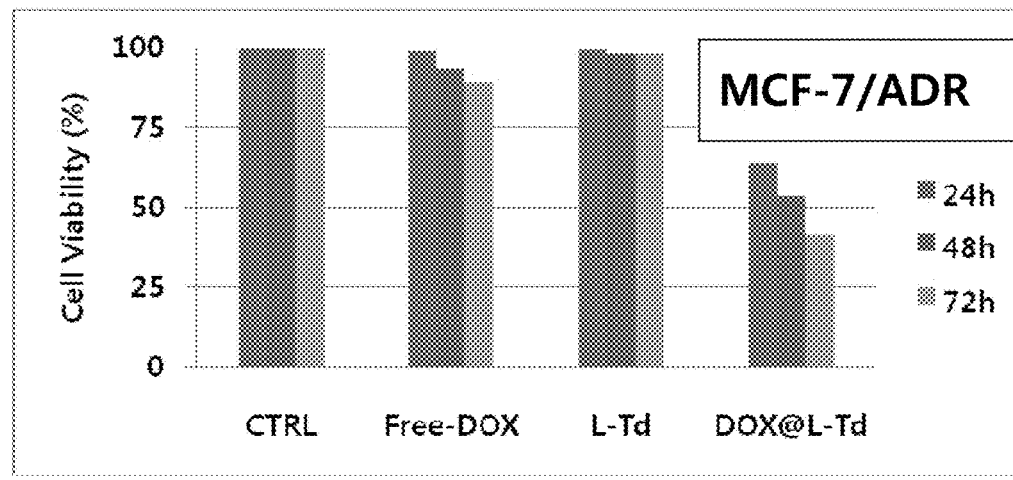

FIG. 7 Cell viability assay result (%) showing the effects of small molecule drug delivery, average of triplicate experiments.

(a) Effects on Drug-sensitive MCF-7 cells.

(b) Effects on Drug-resistant MCF-7/ADR cells. CTRL: control, Free-DOX: free doxorubicin, DOX@Td: doxorubicin-intercalated L-Td.

Figure 8:
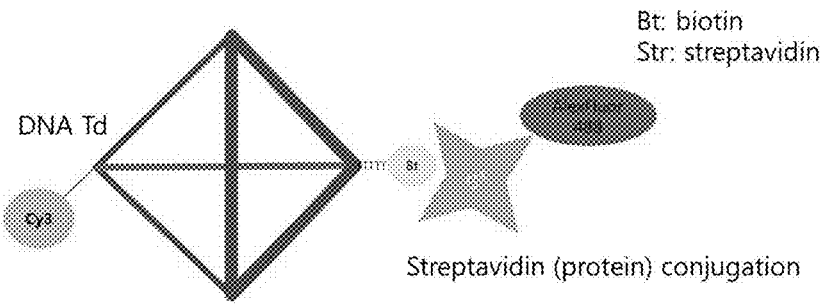
Figure 8:
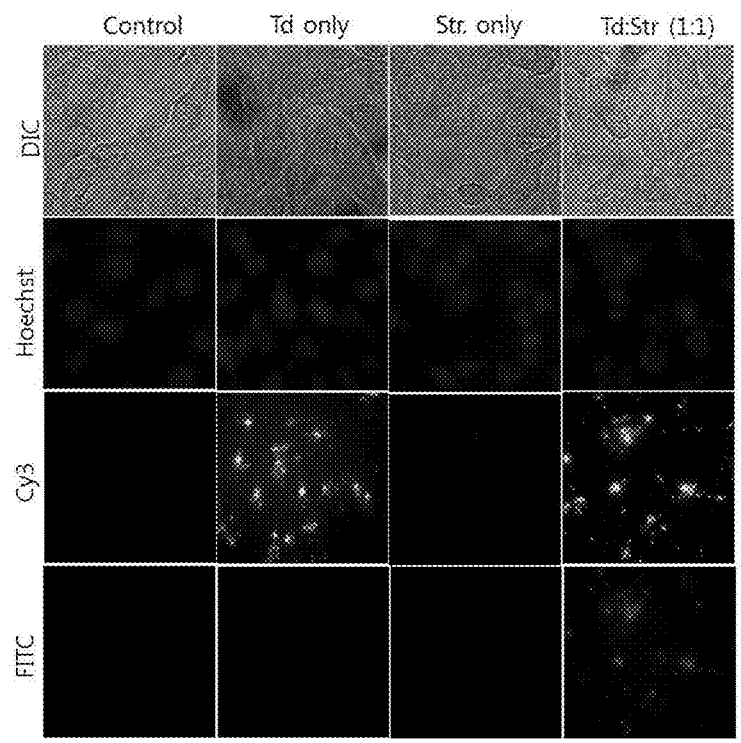
Figure 8:
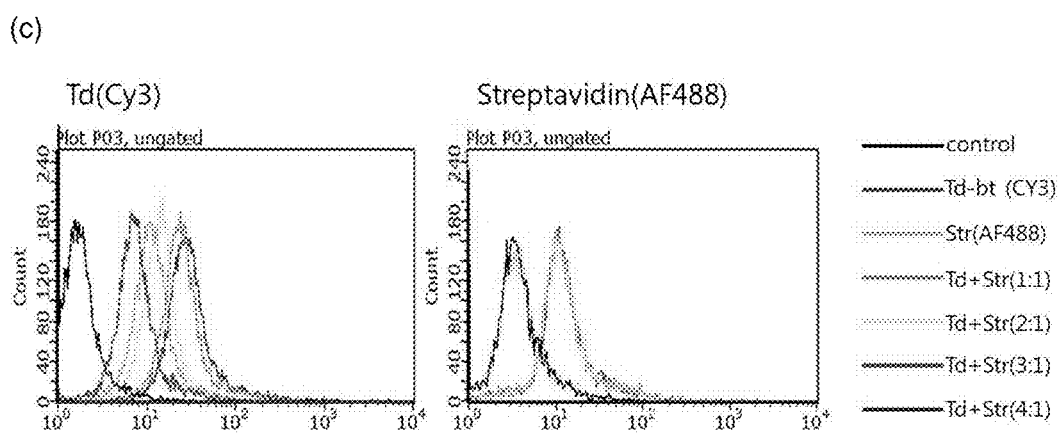

FIG. 8 (a) Schematic diagram of streptavidin (protein) cojugated L-Td.

(b) Cellular uptake of streptavidin conjugated L-Td into cells.

(c) Flow cytometry for cellular uptake.

DETAILED DESCRIPTION OF THE INVENTION

An object of the present invention is to provide a drug carrier to deliver pharmaceutically active ingredient into cells, wherein the drug carrier is L-DNA nanocage construct forming a 3-dimensional cage shape.

Based on the idea that it would be good for a carrier to have a base pair system orthogonal to the natural base-pair system in order to prevent unwanted hybridization or interference between carrier sequence and cargo sequence that might be occurred when the cargo to be delivered into cells are nucleic acids and in order to allow free selection of cargo regardless of the sequence of the nanocarrier, the present inventors have prepared L-DNA nanocage construct using L-DNA as a backbone, and found out that interestingly, L-DNA nanocage construct has a high efficiency of cellular delivery so that it is very suitable to deliver pharmaceutically active ingredients into cells.

The L-DNA used in the drug carrier of the present invention is the mirror form of natural DNA and has the same thermodynamic features as D-DNA in hybridization.

Figure 1:
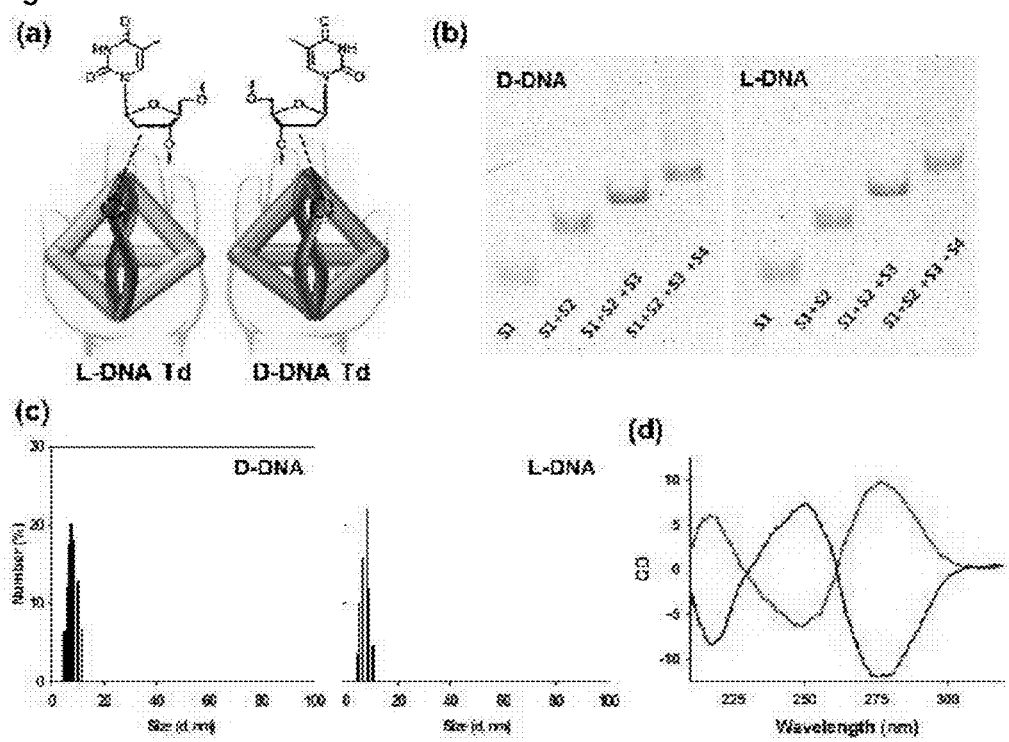
FIG. 1 (a) Diagram of D-DNA tetrahedron (D-Td) and L-DNA tetrahedron (L-Td).

In order to form a constant DNA nanostructure even after replacing the backbone of carrier with orthogonal system, it is required to use orthogonal base pairing system having the same thermodynamic features to those of natural system. Even though some nucleic acids have been known to have orthogonal base pair features, there was no report to show similar thermodynamic stability to that of natural DNA. However, as the L-DNA used in the drug carrier of the present invention shows the same thermodynamic features to those of D-DNA, it can be self-assembled to form a nanocage assembly construct with left-handed helical property (FIG. 1a).

In an example, the drug carrier of the present invention has a merit to show increased cellular uptake efficiency, compared with D-DNA cage construct.

In another example, the drug carrier of the present invention has a merit to show more increased serum stability or nucleotide resistance, compared with D-DNA cage construct.

In another example, the drug carrier of the present invention has a merit able to use any natural nucleic acid-based cargo freely without concern of interference caused by unwanted hybridization between carrier sequence and cargo sequence in case that the cargo is nucleic acid particularly, as L-DNA is used as a backbone of nanocarrier assembly instead of D-DNA.

In the drug carrier of the present invention, L-DNA cage construct has a 3 dimensional cage-like structure formed by self-assembly of common linear DNA, and for example may have various 3D polyhedron structures.

In another example of the present invention, the L-DNA cage construct may have various polyhedron structures such as tetrahedron, hexahedron, octahedron, dodecahedron, icosahedron, and hexakisoctahedron, bipyramids or fullerene like structure, but is not limited thereto.

In a preferable example, the 3 dimensional L-DNA nanocage structure may be tetrahedron.

Among the various 3 dimensional L-DNA cage structures, the L-DNA tetrahedron, particularly, can be assembled simply from 4 L-DNA strands and be prepared in higher yield, so is the most practical.

However, the various 3 dimensional DNA nanocage structures other than the L-DNA tetrahedron also have improved cellular uptake and intracellular stability by having L-DNA backbone, so can be used as a drug carrier to deliver pharmaceutically active ingredients into the cells usefully.

According to an example of the present invention, the pharmaceutically active ingredients may be caught in the L-DNA cage construct of the present invention and delivered into the cells, or may be bound to L-DNA backbone and delivered into the cells.

The pharmaceutically active ingredients, for example, may be caught in the cage construct or bound to the L-DNA backbone by assembly of linear L-DNA strands into 3 dimensional cage structure in state of mixing them with linear L-DNA strands.

Types of the pharmaceutically active ingredients able to be delivered into the cells by using the drug carrier of the present invention are not limited specifically and include anticancer drug, contrast agent, hormone, anti-hormone agent, vitamins, calcium, minerals, sugar agents, organic acid agents, protein amino acids, detoxification agent, enzymatic agent, metabolic agent, diabetes combination agent, tissue revival agent, chlorophyll agent, pigment agent, tumor agent, tumor therapeutic agent, radioactive medicine, tissue cell diagnosis agent, tissue cell therapeutic agent, antibiotic agent, antiviral agent, complex antibiotic agent, chemical agent, vaccine, toxin, toxoid, anti-toxin, Leptospira serum, blood agent, biological agent, analgesic, immunogenic molecule, antihistamine agent, allergic drug, nonspecific immunogenic agent, anesthetic drug, stimulant, psychotropic agent, nucleic acid, aptamer, antisense nucleic acid, oligonucleotide, small molecule drug, protein, peptide, siRNA, and micro RNA.

In a preferable example, the drug carrier of the present invention can be used to deliver nucleic acids as a pharmaceutically active ingredient into the cells and in this case, as there is no concern that the nucleic acid sequence of cargo might be hybridized with the sequence of carrier, it has a merit able to use any natural nucleic acid-based cargo freely.

Another object of the present invention is to provide a pharmaceutical composition for treating cancer comprising the drug carrier with L-DNA nanocage structure, wherein the L-DNA forms 3 dimensional cage, and anticancer drug.

In an example, the anticancer drug is a DNA or RNA aptamer, small molecule drug, or protein or peptide drug.

The anticancer composite of the present invention also includes pharmaceutically acceptable carrier with the said 3-dimensional DNA nanocage structures. The pharmaceutically acceptable carrier is usually used in manufacturing medicine and includes lactose, dextrose, sucrose, sorbitol, mannitol, starch, acasia rubber, calcium phosphate, alginate, gelatin, calcium silicate, microcrystal cellulose, polyvinyl pyrrolidone, cellulose, water, syrup, methyl cellulose, methylhydroxy benzoate, hydroxypropylbenzoate, talcum, magnesium stearate and mineral oil, but is not limited thereto. The suitable pharmaceutically acceptable carrier and agent are described in *Remington's Pharmaceutical Sciences* (19th ed., 1995) in detail.

Effects of Invention

The drug carrier of the present invention having L-DNA nanocage structure prepared using L-DNA, the mirror form of natural DNA, as a backbone has very superior cellular uptake efficiency and serum stability, so can be used helpfully to deliver various drugs into cells.

In addition, the drug carrier of the present invention has a merit able to use any natural nucleic acid-based cargo freely without concern of interference caused by unwanted hybridization between carrier sequence and cargo sequence in case that the cargo is nucleic acid particularly.

The foregoing embodiments and advantages are merely exemplary and are not to be construed as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

EXAMPLE

<Materials and Methods>

1. Synthesis and Purification of Oligonucleotides

All (D/L)-DNA oligonucleotides were synthesized using standard method using oligo synthesizer (Mermaid 4 DNA/RNA synthesizer, Mermaid, USA). And then, these were purified by PAGE and ethanol precipitation.

2. Preparation of D, L-Td Labeled w/ or w/o Aptamer AS1411

Td w/ or w/o aptamer was assembled by mixing FAM-S1, S2, S3, S4 and FAM-S1, S2-A, S3-A, S4-A. Four DNA sequences (250 nM of each sequence) were mixed in TM buffer (10 mM Tris-HCl, 5 mM MgCl2, pH=8). The mixture was denatured by heating to 95° C. and annealed by cooling to 4° C. using RT-PCR machine (Applied Biosystems, USA).

3. Gel Electrophoresis.

Non-denaturing polyacrylamide gels (6%) were run in TBE buffer with 100V at 4° C. for 40 min. After electrophoresis, the images were visualized using a fluorescence scanner (Typhoon 9400, GE healthcare, USA).

4. Dynamic Light Scattering (DLS)

The size of D, L-Td w/ or w/o AS1411 was measured in Zetasizer (Malvern, UK). Concentration of sample was 250 nM (40 µL).

5. Transfection of DNA Nanoconstructs into HeLa and NIH3T3 Cells

HeLa cells (cancer cell line) and NIH3T3 cells (normal cell line as a control) were plated in glass bottomed 35 mm dishes with DMEM medium (Gibco, USA) containing 10% heat inactivated fetal bovine serum, 1% penicillin and streptomycin. After 25000 cells were seeded in each dish, the dishes were incubated at 37° C., in humidified atmosphere containing 5% $CO_2$. The growth medium was removed from each cell sample, and the cells were washed twice with PBS (Gibco, USA). Each transfection mixture was made using D, L-Td w/ or w/o AS1411 (250 nM) in the fresh medium (250 µL) without serum and antibiotics. Final concentration of DNA samples were 10 nM.

6. Microscopic Imaging of Td in Cells

The nuclei were stained using Hoechst 34580 (3 µg/mL, Invitrogen, USA), and the cells were washed with PBS (200 µL) twice. The cell culture medium (200 µL) was then added. Live cells were imaged using a fluorescence microscopy (DeltaVision, Applied Precision, USA). Excitation/emission filters used for fluorescein and Hoechst 34580 were 480-500/509-547 nm, and 340-380/432-482 nm, respectively.

7. Flow Cytometry Analysis.

HeLa cells and NIH-3T3 cells were seeded on 24-well culture plates at a density of $10^5$ cells/mL and cultured for 24 h and then washed twice with PBS. They were incubated with the fluorescently labeled DNA molecules by using the same method adopted for the transfection experiment, harvested, and washed three times with PBS. Then, 200 µl of trypsin replacement (TrypLE™, Gibco, USA) was added to each sample, and the samples were incubated for 5 min at 37° C. Then 1 mL of the medium was added to each sample, and the resulting cell suspensions were transferred to conical tubes (Falcon™ tubes, BD Biosciences, USA) and centrifuged for 2 min at 1200 rpm. Supernatant was removed, and the cell pellets were resuspended in 1 mL of PBS. Fluorescence intensity of the cells was estimated by flow cytometry (FC500, Beckman coulter, USA). Fluorescence intensity of the cells was estimated by flow cytometry (FC500, Beckman coulter, USA). Samples of at least 1000 cells were analyzed in triplicate.

8. Nuclease Resistance

For the stability test, 10% mouse serum (10 µL, Sigma Aldrich, USA) were added to the DNA solutions (90 µL, 900 nM), and the mixture were incubated at 37° C. At each point, the solutions were quenched by adding the stop solution composed of 98% deionized formamide, 10 mM EDTA, 0.5 mg/ml bromophenol blue and xylenecyanole, and then analyzed on a denaturing 12% PAGE (7M UREA). The amount of undamaged DNA structures was estimated by visualization of FAM-S1 on a fluorescence scanner (Typhoon9400, GE Healthcare, USA).

9. Endocytosis Assay

HeLa cells ($2 \times 10^5$ cells/well) were seeded with DMEM media (2 mL) on a 6-well plate and incubated overnight at 37° C. in humidified atmosphere containing 5% CO2. For the treatment of inhibitors, the media were replaced with the fresh medium (2 mL) containing amiloride (2 mM, an inhibitor for macropinocytosis), chloroproamzine (10 µg/mL, CPZ, an inhibitor for clathrin-mediated endocytosis), or genistein (200 µM, an inhibitor for caveolae-mediated endocytosis). After 30 min, Td (10 nM) was added into the cell media and incubated at 37° C. for 2 h. After washing with PBS, the cells were trypsinized, centrifuged and lysed in RIPA buffer, and fluorescence intensity of Cy5 labeled on Td was measured using an fluorescence microplate reader (Appliskan™, Thermo Fisher Scientific, USA) for quantitation of intracellularly delivered Td via endocytosis. The amount of Td in cell lysates was normalized to the total cellular protein content of cells, which was determined by protein assay kit (BIO-RAD, Hercules, Calif., USA).

10. Cell Viability Assays (D, L-Td Labeled w/ or w/o Aptamer AS1411)

Cytotoxicity of D, L-Td labeled w/ or w/o aptamer AS1411 was estimated using an MTT assay. Briefly, $8 \times 10^3$ HeLa cells (cancer cell line) and NIH-3T3 cells (normal cell line as a control) were seeded with media (100 µL) in 96-well plates and cultured overnight to reach ~80% confluency. The cells were then incubated in the fresh media containing DNA molecules at 37° C. for 6 h in the $CO_2$ chamber. For multivalent effect by AS1411 tag, alternatively, the cells were incubated in fresh media containing AS1411 monomer was incubated at same conditions. Then, washed twice using DPBS, and changed the cell culture media containing 10% FBS and 1% antibiotics, and incubated for 48 h at 37° C., in humidified atmosphere containing 5% $CO_2$ After that, thiazolyl blue tetrazolium bromide (MTT, TACS, Germany) solution (10 μL) was added to each well, followed by 4 h incubation at 37° C. Next, cells were lysed with 200 μL of dimethyl sulfoxide (DMSO, Sigma-Aldrich, USA). After overnight incubation at room temperature, the absorbance was measured at 580 nm using a microplate reader (SpectraMax Plus™, Molecular Devices, USA).

11. Cell Viability Assays (Small Molecule Drug Delivery)

Preparation of DOX@Td (Doxorubicin-Intrecalated L-Td):

For DOX intercalation into the Cy5-labeled Td, DOX (1 mM) was mixed with the fluorescent DNA tetrahedron (10 μM) for 1 h and then run through NAP10 (G25-DNA grade column, GE Healthcare, USA) to remove the free DOX remaining in solution. The number of intercalated DOX molecules per DNA tetrahedron was calculated using the extinction coefficient of Cy5 at 633 nm (ε=230400) and that of DOX at 480 nm (ε=10410), respectively.

Cell Viability Assays:

Drug-sensitive MCF-7 cells and drug-resistant MCF-7/ADR cells were used for cell viability assays. Cytotoxicity of Td was estimated using an MTT assay. Briefly, 8×10³ mammalian cells were seeded with media (100 μL) in 96-well plates and cultured overnight to reach ~80% confluency. The cells were then incubated in the fresh media containing Td at 37° C. for 6 h in the $CO_2$ chamber. For cytotoxicity by the DOX treatment, alternatively, the cells were incubated in fresh media containing free DOX or DOX@Td were incubated at 37° C. for 24 h in the $CO_2$ chamber. Then, thiazolyl blue tetrazolium bromide (MTT, TACS, Germany) solution (10 μL) was added to each well, followed by 4 h incubation at 37° C. Next, cells were lysed with 200 μL of dimethyl sulfoxide (DMSO, Sigma-Aldrich, USA). After overnight incubation at room temperature, the absorbance was measured at 580 nm using a microplate reader (SpectraMaxPlus™, Molecular Devices, USA).

12. Fluorescence Microscopy & Flow Cytometry (Protein Delivery)

Transfection of L-Td-Streptavidin Conjugate into HeLa Cells:

HeLa cells were plated in glass-bottomed 35 mm petri dishes with RPMI1640 media (Gibco, USA) containing 10% heat inactivated fetal bovine serum, 1% penicillin and streptomycin. After cells (2.5×10⁴) were seeded in each dish, the dishes were incubated overnight at 37° C. in humidified atmosphere containing 5% $CO_2$. Growth medium was removed from each cell sample, and the cells were washed twice with PBS (Gibco, USA). L-Td-streptavidin conjugate (10 nM, prepared by mixing L-Td and streptavidin with 1:1 ratio) in fresh media (250 μL) lacking serum and the antibiotics was then added to a sample of cells and incubated for 6 h at 37° C. in humidified atmosphere containing 5% $CO_2$. Cells then were washed twice with PBS and used for microscopic and flow cytometric experiments.

<Results>

1. Preparation of L-, D-DNA Tetramer Construct

The DNA oligonucleotides required for construction of Tds were synthesized by using standard protocols in a DNA synthesizer. The base sequences of DNA strands were adopted from the Tuberfield's Td. Below table 1 shows DNA sequences used in the examples, wherein L-DNA sequence was indicated with underline and the linker portion in italics.

TABLE 1

| Name | Sequence |
|---|---|
| S1 (D) | ACATTCCTAAGTCTGAAACATTACAGCTTGCTACACGAGAAGAGCCGCCATAGTA-fluorescein |
| S2 (D) | *TTTTTT*ATCACCAGGCAGTTGACAGTGTAGCAAGCTGTAATAGATGCGAGGGTCCAATACTT-NH₂ |
| S3 (D) | *TTTTTT*CAACTGCCTGGTGATAAAACGACACTACGTGGGAATCTACTATGGCGGCTCTTC-NH₂ |
| S4 (D) | *TTTTTTT*CAGACTTAGGAATGTGCTTCCCACGTAGTGTCGTTTGTATTGGACCCTCGCAT-NH₂ |
| S1 (L) | <u>ACATTCCTAAGTCTGAAACATTACAGCTTGCTACACGAGAAGAGCCGCCATAGTA</u>-fluorescein |
| S2 (L) | *TTTTTT*<u>ATCACCAGGCAGTTGACAGTGTAGCAAGCTGTAATAGATGCGAGGGTCCAATACTT</u>-NH₂ |
| S3 (L) | *TTTTTT*<u>CAACTGCCTGGTGATAAAACGACACTACGTGGGAATCTACTATGGCGGCTCTTC</u>-NH₂ |
| S4 (L) | *TTTTTTT*<u>CAGACTTAGGAATGTGCTTCCCACGTAGTGTCGTTTGTATTGGACCCTCGCAT</u>-NH₂ |
| S2 (D)-Ap | GGTGGTGGTGGTTGTGGTGGTGGTGGTTTTTTATCACCAGGCAGTTGACAGTGTAGCAAGCTGTAATAGATGCGAGGGTCCAATACTT-NH₂ |
| S3 (D)-Ap | GGTGGTGGTGGTTGTGGTGGTGGTGGTTTTTTCAACTGCCTGGTGATAAAACGACACTACGTGGGAATCTACTATGGCGGCICITC-NH₂ |
| S4 (D)-Ap | GGTGGTGGTGGTTGTGGTGGTGGTGGTTTTTTTCAGACTTAGGAATGTGCTTCCCACGTAGTGTCGTTTGTATTGGACCCTCGCAT-NH₂ |
| S2 (L)-Ap | GGTGGTGGTGGTTGTGGTGGTGGTGG<u>TTTTTTATCACCAGGCAGTTGACAGTGTAGCAAGCTGTAATAGATGCGAGGGTCCAATACTT</u>-NH₂ |
| S3 (L)-Ap | GGTGGTGGTGGTTGTGGTGGTGGTGG<u>TTTTTTCAACTGCCTGGTGATAAAACGACACTACGTGGGAATCTACTATGGCGGCTCTTC</u>-NH₂ |
| S4 (L)-Ap | GGTGGTGGTGGTTGTGGTGGTGGTGG<u>TTTTTTTCAGACTTAGGAATGTGCTTCCCACGTAGTGTCGTTTGTATTGGACCCTCGCAT</u>-NH₂ |

The Td assembly without aptamer attachment was performed by following the previously reported procedure (Goodman, R. P.; Berry, R. M.; Turberfield, A. J. *Chem. Commun.* 2004, 40, 1372-1373). The construction of self-assembled D and L-Td was verified on 6% non-denaturing polyacrylamide gel electrophoresis (PAGE) (FIG. 1b). Both D- and L-Td showed the same sequential retardation pattern as the number of DNA strands participating in the assembly increased, suggesting that L-Td could be formed under the same condition required for the assembly of D-Td.

Hydrodynamic sizes of D- and L-Td were 7.63 (±0.37) nm and 7.80 (±0.31) nm, respectively (FIG. 1c), as determined by dynamic light scattering (DLS).

When CD spectra of Tds were measured, a typical profile for a right-handed DNA helix was observed from D-Td presenting a negative peak around 254 nm and a positive peak around 270 nm, whereas the symmetrical mirror spectrum was observed from L-Td, indicating that L-Td was formed with the left-handed helical property as expected (FIG. 1d).

2. Assessment of Cellular Uptake and Nuclease Resistance of D-, L-Td

It has been reported that D-Td could be internalized into mammalian cells via endocytosis. In order to investigate the influence of the backbone on this cellular uptake property of Td, cellular uptake efficiency of L-Td was also examined and compared with that of D-Td. After incubation of both fluorescently labeled D-Td and L-Td either with cancer cells (HeLa) or with normal cells (NIH-3T3) in the absence of any transfection reagent, fluorescence microscopic images were obtained. Higher fluorescence intensity was observed in the cells treated with L-Td than in those with D-Td, which suggests that L-Td could be delivered more efficiently than D-Td (FIG. 2a).

Quantitative analysis based on flow cytometry showed that intracellular delivery of L-Td was about 2.5-fold higher in the cancer cell line and 3-fold higher in the normal cell line than the internalization of D-Td, respectively (FIG. 2b). This result was consistent with the microscopic images.

Previously, we have reported that non-clathrin-mediated endocytosis mechanisms were involved with the uptake of D-Td.[1] A test using three endocytosis inhibitors to verify the delivery mechanism for L-Td revealed that the enhanced uptake of L-Td compared to D-Td was achieved through the mechanisms including not only non-clathrin-mediated but also clathrin-mediated endocytosis (FIG. 2c).

The effect of the mirror backbone on nuclease resistance was also examined in 10% mouse serum. In contrast to D-Td which could hardly survive after 10 h exposure to the serum solution, L-Td was conserved without degradation by nucleases under the same condition, showing invulnerability against the enzymes in serum for several hours (FIG. 3).

Increased nuclease resistance gained with the Td assembly seemed to be additionally improved due to the unnatural sugar backbone in L-Td. This long term serum stability of the L-DNA backbone would potentially be advantageous when it is used as a carrier in intravenous delivery for in vivo applications.

3. Preparation of D-, L-Td with Aptamer

After observing useful properties of L-Td as a delivery carrier in comparison with D-Td such as enhanced cellular uptake and higher serum stability, we attempted to assemble aptamer-attached Tds by adopting the DNA strands containing the sequence of an anti-proliferative aptamer, AS1411 at one end (FIG. 4a and Table 1).

Based on the same manner used for construction of D- and L-Td, preparation of DNA tetrahedra containing one to three aptamers were purchased. According to the gel electrophoresis analysis, no distinct band indicating an aptamer-attached self-assembly structure was observed with the D-Td backbone (Ap1-D-Td, Ap2-D-Td, and Ap3-D-Td), suggesting that the D-Td construct was not created properly with the aptamer-labeled DNA strands (FIG. 4b, left).

Aptamer constructs with L-DNA strands (Ap1-L-Td, Ap2-L-Td, and Ap3-L-Td), however, lead to clear bands with retarded mobility compared to the band of L-Td itself, implying that self-assembled Td structures were maintained even with the dangling aptamers (FIG. 4b, right).

These results demonstrate that the unsuccessful assembly of Ap-D-Tds resulted from the undesired base-pairing between the aptamer moiety and the sequence required for the tetrahedron structure. They also implicated that the cross-interaction based on partial base complementary between the aptamer and the D-Td skeleton do not exist in the L-Td case, because of the backbone orthogonality. In contrast to the size similarity between D-Td and L-Td, the sizes of Ap3-D-Td (10.9±0.44 nm) and Ap3-L-Td (8.93±0.21 nm) were considerably different from each other in DLS measurement (FIG. 5). The size increase in Ap3-D-Td might be due to failure to construct compactly self-assembled structures, consistent with the gel analysis data.

4. Assessment of Cellular Uptake of D-, L-Td with Aptamer

To investigate whether organization of aptamers on Tds influences on the cellular uptake of DNA nanoconstructs, microscopic images of both cancer cells and normal cells were acquired after treatment of the cells with the aptamer-attached Tds. Ap3-L-Td possessing well-organized multivalent aptamers provided higher uptake signals than Ap3-D-Td (FIG. 4c). The difference in the uptake efficiency between L- and D-based constructs was greater in the cancer cell line. This is likely due to the multivalent interaction between aptamers on L-Td and nucleolin, the target protein expressed on the surface of malignant cells. In addition, the Td construct also apparently contributed to the cellular uptake since the free aptamer was less delivered into cells than the single aptamer-labeled Tds. The analysis by flow cytometry exhibited that the delivery efficiency was improved in proportional to the number of aptamers on L-Td. In contrast, the efficiency was not affected by the number of aptamers on D-Td.

5. Assessment of Anti-Proliferative Effect of D-, L-Td with Aptamer

The anti-proliferative effect by the multivalent aptamers on L-Td was examined by using cell viability assays. Although all the aptamer-loaded Tds displayed dose-dependent toxicity in the cancer cell line at a certain level, the potency varied depending on the number of aptamers on Td and the backbone type of the DNA nanocarriers. Potency of Ap-L-Tds was higher than that of Ap-D-Tds in general and increased with the number of aptamers attached. Ap3-L-Td showed the highest potency leading to about 50% of HeLa cells viable after treatment only with 500 nM of the trivalent aptamer on L-Td (FIG. 6a). However, more than 95% of the cells survived at the same concentration of the free AS1411 aptamer which have its $EC_{50}$ value about at 30 μM, demonstrating that higher potency of Ap3-L-Td was obtained from higher uptake of aptamers based on the multivalent effect. Well-organized display of multivalent aptamers is likely to be important in delivery of aptamers and the subsequent downstream efficacy in cells, since irregularly arranged aptamers in Ap-D-Tds were not as potent as those in Ap-L-Tds. Besides of known stability of the AS1411 aptamer in serum, enhanced serum stability of L-Td also possibly contributed to the high potency of Ap-L-Tds. The moderately improved potency of Ap3-D-Td compared to that of Ap1-D-Td and Ap2-D-Td may well be due to the higher aptamer portion in the construct. When incubated with the normal cells, all Tds exhibited significantly decreased cytotoxicity (FIG. 6b). Interestingly, Ap3-D-Td was slightly more cytotoxic than Ap3-L-Td in the normal cells, even though they were delivered at the similar level. This might be due to unexpected off-target effect in cells raised by its mis-assembled structures. In comparison with the free aptamer, single aptamer-attached Tds provided higher cytotoxicity in the cancer cells, which is probably due to the uptake efficiency boosted by Td. Td itself with either D- or L-backbone, however, did not influence on cell viability, proving that the DNA nanoconstructs themselves are non-cytotoxic. Thus, the cytotoxicity of aptamer-loaded Tds resulted solely from the aptamer moiety.

In conclusion, we have newly prepared a DNA tetrahedron based on L-sugar backbone. Compared with the natural D-sugar-based one, L-Td could be more easily delivered without using any transfection agent and showed higher nuclease resistance in serum. Utilizing the base-paring orthogonality between D-DNA and L-DNA, we could successfully assemble aptamer-loaded L-Tds whereas failed to construct well-defined aptamer-attached D-Tds due to the cross-interaction between the bases in aptamer and those in D-Td. Compared with the free aptamer, the trivalent aptamers arranged on L-Td found to be 60-fold more potent cytotoxic effect only against cancer cells, possibly because of enhanced uptake specifically into cancer cells which display the target protein of the aptamer on the cell surface. In addition, proper arrangement of multivalent aptamers also contributed to their targeted potency, maximizing desired cytotoxicity in cancer cells and minimizing undesired cytotoxicity in normal cells. Although DNA tetrahedra have been proved to be useful drug carriers with excellent biocompatibility and low cytotoxicity in previous studies, we have demonstrated that nucleotide-based cargos have a potential to disturb the self-assembly of DNA nanoconstructs in this study. Therefore, our strategy employing L-DNA-based nanocarriers for delivery of therapeutic nucleic acids without affecting thermodynamic property of the assembly would be a promising solution to circumvent the problematic situation stemming from the disruption of desired base-pairing.

6. Assessment of Anti-Proliferative Effect of L-Td with Small Molecule Drug (Small Molecule Drug Delivery)

The anti-proliferative effects by control, Free-Dox, L-Td and DOX@Td (doxorubicin-intrecalated L-Td) were examined through cell viability assays using drug-sensitive MCF-7 cells and drug-resistant MCF-7/ADR cells. Below table 2 shows the experimental results.

TABLE 2

Cell viability assay (%). Average of triplicate experiments

|  | CTRL | Free-DOX | L-Td | DOX@L-Td |
|---|---|---|---|---|
| MCF-7 | | | | |
| 24 h | 100 | 75.2 | 99.7 | 63.2 |
| 48 h | 100 | 71.3 | 98.9 | 51.1 |
| 72 h | 100 | 67.5 | 99.2 | 40.9 |
| MCF-7/ADR | | | | |
| 24 h | 100 | 98.9 | 99.4 | 64.1 |
| 48 h | 100 | 93.6 | 98.1 | 53.8 |
| 72 h | 100 | 89.2 | 98.3 | 41.5 |

DOX@Td showed higher potency than that of Free-DOX in general and also displayed excellent toxicity in MCF-7/ADR as well as MCF-7 (FIGS. 7 (a) and (b)).

7. Assessment of Cellular Uptake of L-Td with Protein (Protein Delivery)

To investigate whether conjugation of protein drug on Tds influences on the cellular uptake of DNA nanoconstructs, microscopic images were acquired after treatment of the cells with the protein-attached Tds. Streptavidin (protein) cojugated L-Td provided higher uptake signals as confirmed in FIGS. 8b and 8c.

What is claimed is:

1. A drug carrier for delivering a pharmaceutically active ingredient into cells,
   wherein the drug carrier is a L-DNA cage construct having a self-assembled 3-D nucleic acid nanostructure;
   wherein the L-DNA cage construct is self-assembled from 4 L-DNA single strand nucleic acids, wherein the single strands hybridize to form double stranded nucleic acids;
   wherein the double stranded hybridized nucleic acids form the sides of the self-assembled 3-D nucleic acid nanostructure;
   and the single strands consist of at least two distinct nucleotide sequences selected from the group consisting of SEQ ID NOs: 5, 6, 7 and 8.

2. The drug carrier of claim 1, wherein the L-DNA cage construct has a tetrahedron structure.

3. The drug carrier of claim 1, wherein the drug carrier further comprises a pharmaceutically active ingredient, and wherein the pharmaceutically active ingredient is selected from anticancer drug, contrast agent, nucleic acid, aptamer, antisense nucleic acid, oligonucleotide, small molecule drug, protein, peptide, siRNA and micro RNA.

4. The drug carrier of claim 1, wherein the drug carrier further comprises a pharmaceutically active ingredient, and wherein the pharmaceutically active ingredient is nucleic acid, small molecule drug, protein drug or peptide drug.

5. The drug carrier of claim 1, wherein the drug carrier further comprises a pharmaceutically active ingredient, and wherein the pharmaceutically active ingredient is delivered into cells by being caught within the L-DNA cage construct or bound to the L-DNA backbone.

6. The drug carrier of claim 1, wherein the carrier has more increased cellular uptake efficiency than the corresponding D-DNA cage construct.

7. The drug carrier of claim 1, wherein the carrier has more increased nuclease resistance compared with a corresponding D-DNA cage construct.

8. A pharmaceutical composition for treating cancer comprising the drug carrier of claim 1 and an anticancer drug.

9. The pharmaceutical composition of claim 8, wherein the anticancer drug is a DNA aptamer, RNA aptamer, small molecule drug, protein drug or peptide drug.

10. The drug carrier of claim 1, wherein the 5' terminal nucleic acid end and/or 3' terminal nucleic acid end of each single strand is disposed on the sides of the vertices of the L-DNA cage construct.

11. The pharmaceutical composition of claim 8, wherein the anticancer drug is doxorubicin.

* * * * *

SEQUENCE LISTING

```
<160> NUMBER OF SEQ ID NOS: 14

<210> SEQ ID NO 1
<211> LENGTH: 55
<212> TYPE: DNA
<213> ORGANISM: Artificial Sequence
<220> FEATURE:
<223> OTHER INFORMATION: A DNA sequence used in constructing
      tetrahedrons in the working examples - S1 (D)

<400> SEQUENCE: 1
acattcctaa gtctgaaaca ttacagcttg ctacacgaga agagccgcca tagta         55

<210> SEQ ID NO 2
<211> LENGTH: 62
<212> TYPE: DNA
<213> ORGANISM: Artificial Sequence
<220> FEATURE:
<223> OTHER INFORMATION: A DNA sequence used in constructing
      tetrahedrons in the working examples - S2 (D)

<400> SEQUENCE: 2 tttttatca ccaggcagtt gacagtgtag caagctgtaa tagatgcgag ggtccaatac    60
tt                                                                  62

<210> SEQ ID NO 3
<211> LENGTH: 60
<212> TYPE: DNA
<213> ORGANISM: Artificial Sequence
<220> FEATURE:
<223> OTHER INFORMATION: A DNA sequence used in constructing
      tetrahedrons in the working examples - S3 (D)

<400> SEQUENCE: 3 tttttcaac tgcctggtga taaaacgaca ctacgtggga atctactatg gcggctcttc    60
```

```
<210> SEQ ID NO 4
<211> LENGTH: 60
<212> TYPE: DNA
<213> ORGANISM: Artificial Sequence
<220> FEATURE:
<223> OTHER INFORMATION: A DNA sequence used in constructing
      tetrahedrons in the working examples - S4 (D)

<400> SEQUENCE: 4
tttttttcag acttaggaat gtgcttccca cgtagtgtcg tttgtattgg accctcgcat     60

<210> SEQ ID NO 5
<211> LENGTH: 55
<212> TYPE: DNA
<213> ORGANISM: Artificial Sequence
<220> FEATURE:
<223> OTHER INFORMATION: A DNA sequence used in constructing
      tetrahedrons in the working examples - S1 (L)

<400> SEQUENCE: 5
acattcctaa gtctgaaaca ttacagcttg ctacacgaga agagccgcca tagta          55

<210> SEQ ID NO 6
<211> LENGTH: 62
<212> TYPE: DNA
<213> ORGANISM: Artificial Sequence
<220> FEATURE:
<223> OTHER INFORMATION: A DNA sequence used in constructing
      tetrahedrons in the working examples - S2 (L)

<400> SEQUENCE: 6 tttttttatca ccaggcagtt gacagtgtag caagctgtaa tagatgcgag ggtccaatac    60
tt                                                                    62

<210> SEQ ID NO 7
<211> LENGTH: 60
<212> TYPE: DNA
<213> ORGANISM: Artificial Sequence
<220> FEATURE:
<223> OTHER INFORMATION: A DNA sequence used in constructing
      tetrahedrons in the working examples - S3 (L)

<400> SEQUENCE: 7 tttttttcaac tgcctggtga taaaacgaca ctacgtggga atctactatg gcggctcttc    60

<210> SEQ ID NO 8
<211> LENGTH: 60
<212> TYPE: DNA
<213> ORGANISM: Artificial Sequence
<220> FEATURE:
<223> OTHER INFORMATION: A DNA sequence used in constructing
      tetrahedrons in the working examples - S4 (L)

<400> SEQUENCE: 8
tttttttcag acttaggaat gtgcttccca cgtagtgtcg tttgtattgg accctcgcat     60

<210> SEQ ID NO 9
<211> LENGTH: 88
<212> TYPE: DNA
<213> ORGANISM: Artificial Sequence
<220> FEATURE:
<223> OTHER INFORMATION: A DNA sequence used in constructing
      tetrahedrons in the working examples - S2 (D)-Ap

<400> SEQUENCE: 9
ggtggtggtg gttgtggtgg tggtggtttt ttatcaccag gcagttgaca gtgtagcaag     60
```
ctgtaataga tgcgagggtc caatactt                                          88

<210> SEQ ID NO 10
<211> LENGTH: 86
<212> TYPE: DNA
<213> ORGANISM: Artificial Sequence
<220> FEATURE:
<223> OTHER INFORMATION: A DNA sequence used in constructing
      tetrahedrons in the working examples - S3 (D)-Ap

<400> SEQUENCE: 10
ggtggtggtg gttgtggtgg tggtggtttt ttcaactgcc tggtgataaa acgacactac       60
gtgggaatct actatggcgg ctcttc                                            86

<210> SEQ ID NO 11
<211> LENGTH: 86
<212> TYPE: DNA
<213> ORGANISM: Artificial Sequence
<220> FEATURE:
<223> OTHER INFORMATION: A DNA sequence used in constructing
      tetrahedrons in the working examples - S4 (D)-Ap

<400> SEQUENCE: 11
ggtggtggtg gttgtggtgg tggtggtttt tttcagactt aggaatgtgc ttcccacgta       60
gtgtcgtttg tattggaccc tcgcat                                            86

<210> SEQ ID NO 12
<211> LENGTH: 88
<212> TYPE: DNA
<213> ORGANISM: Artificial Sequence
<220> FEATURE:
<223> OTHER INFORMATION: A DNA sequence used in constructing
      tetrahedrons in the working examples - S2 (L)-Ap

<400> SEQUENCE: 12
ggtggtggtg gttgtggtgg tggtggtttt ttatcaccag gcagttgaca gtgtagcaag       60
ctgtaataga tgcgagggtc caatactt                                          88

<210> SEQ ID NO 13
<211> LENGTH: 86
<212> TYPE: DNA
<213> ORGANISM: Artificial Sequence
<220> FEATURE:
<223> OTHER INFORMATION: A DNA sequence used in constructing
      tetrahedrons in the working examples - S3 (L)-Ap

<400> SEQUENCE: 13
ggtggtggtg gttgtggtgg tggtggtttt ttcaactgcc tggtgataaa acgacactac       60
gtgggaatct actatggcgg ctcttc                                            86

<210> SEQ ID NO 14
<211> LENGTH: 86
<212> TYPE: DNA
<213> ORGANISM: Artificial Sequence
<220> FEATURE:
<223> OTHER INFORMATION: A DNA sequence used in constructing
      tetrahedrons in the working examples - S4 (L)-Ap

<400> SEQUENCE: 14
ggtggtggtg gttgtggtgg tggtggtttt tttcagactt aggaatgtgc ttcccacgta       60
gtgtcgtttg tattggaccc tcgcat                                            86